United States Patent
Chiou

(10) Patent No.: US 6,836,693 B1
(45) Date of Patent: Dec. 28, 2004

(54) METHOD TO PREDICT DIELECTRIC FILM PROPERTIES USING CHEMICAL BONDING MEASUREMENTS AS INPUT TO COMPUTER MODELING

(75) Inventor: Hung-Wen Chiou, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 840 days.

(21) Appl. No.: 09/624,023

(22) Filed: Jul. 24, 2000

(51) Int. Cl.[7] ............................................. G06F 19/00
(52) U.S. Cl. ..................... 700/121; 700/29; 700/108; 703/13; 703/14
(58) Field of Search ..................... 700/121, 95, 108, 700/109, 110, 29; 324/456; 703/13, 14; 708/402, 821

(56) References Cited

U.S. PATENT DOCUMENTS

| | | | |
|---|---|---|---|
| 5,386,507 A | 1/1995 | Teig et al. ................. | 395/161 |
| 5,687,090 A | 11/1997 | Chen et al. ................ | 364/496 |
| 6,008,906 A | 12/1999 | Maris ........................ | 356/432 |
| 6,326,792 B1 * | 12/2001 | Okada ........................ | 324/456 |

* cited by examiner

Primary Examiner—Leo Picard
Assistant Examiner—Charles Kasenge
(74) Attorney, Agent, or Firm—George O. Saile; Stephen B. Ackerman

(57) ABSTRACT

A new computer based method is provided for the evaluation of dielectric film properties. These properties are for a given dielectric derived from measurements of the chemical bonding of that dielectric. Previously collected reference data are maintained in a reference data base from where data are extracted and used as input to mathematical modeling software that predicts thin film properties. The output of these prediction algorithms is used, together with chemical bonding measurements of the dielectric that is being investigated, as input to a program that computers the dielectric properties of the dielectric.

18 Claims, 10 Drawing Sheets

METHOD TO PREDICT DIELECTRIC FILM PROPERTIES USING CHEMICAL BONDING MEASUREMENTS AS INPUT TO COMPUTER MODELING

BACKGROUND OF THE INVENTION (1) Field of the Invention

The invention relates to the fabrication of integrated circuit devices, and more particularly, to a method for determining dielectric film properties. The method of the invention uses computer modeling of dielectric film properties whereby chemical bonding measurements are the input data that are provided to the computer model.

(2) Description of the Prior Art

Dielectric materials are arguably one of the most frequently applied materials in the creation of semiconductor devices. A wide range of materials can be used as a dielectric material, such materials can for instance contain silicon dioxide ("oxide", doped or undoped) or silicon nitride ("nitride"), silicon oxynitride, fluoropolymer, parylene, polyimide, tetra-ethyl-ortho-silicate (TEOS) based oxides, boro-phosphate-silicate-glass (BPSG), phospho-silicate-glass (PSG), boro-silicate-glass (BSG), Pxide-nitride-oxide (ONO), a low dielectric constant material, such as hydrogen silsesquioxane and HDP-FSG (high-density-plasma fluorine-doped silicate glass. The most commonly used and therefore the preferred dielectrics are silicon dioxide (doped or undoped), silicon oxynitride, parylene or polyimide, spin-on-class, plasma oxide or LPCVD oxide. The preferred dielectric material to be used for the invention is $SiO_2$. Typical conditions for the deposition of a layer of dielectric uses, for instance, PECVD procedures at a temperature of between about 350 and 450 degrees C. to a thickness between about 5000 and 10,000 Angstrom using TEOS as a source. The preferred etching conditions for the TEOS etch are using $CF_4$ or $CHF_3$ as the etchant gas at a flow rate of about 15 sccm, gas pressure about 800 mTorr, rf power density about 400 Watts, with no magnetic field applied, ambient wafer temperature with a time of the etch of about 10 seconds. One of the more interesting dielectric materials that has received increased attention and application is conventional polyimides, which have a number of attractive characteristics for their application in a semiconductor device structure such as the ability to fill openings of high aspect ratio, a relatively low dielectric constant (about 3.2), a simple process required for the depositing of a layer of polyimide, the reduction of sharp features or steps in the underlying layer, high temperature tolerance of cured polyimide. Photosensitive polyimides have these same characteristics but can, in addition, be patterned like a photoresist mask and can, after patterning and etching, remain on the surface on which it has been deposited to serve as a passivation layer. The process of depositing and patterning polyimide is relatively simple and is well understood in the art. Polyimide is typically spun on in the form of a liquid (polyamic-acid precursor). After spin-on, the polyimide may be cured whereby the spun-on polyimide becomes a solid polyimide film. Etching of the cured film often uses oxygen or fluorine based plasma. Polyimide is typically applied over the entire substrate followed by a baking step to cure and evaporate the solvents in the polyimide. Curing of the polyimide provides extra protection to the device circuitry. This step is typically a high temperature cure, at 350 to 400 degrees C., in a $N_2$ gas ambient for a time period between about 1.5 and 2.5 hours. Polyimide provides extra protection to the surface of the silicon chip against scratching, cracking and other types of mechanical damage. Most often, mechanical damage occurs during assembly, packaging or any subsequent handling of the die. As a passivation layer, polyimide also guards against thin film cracking which frequently results from the packaging of very large dies into plastic packages. A passivation layer can contain silicon oxide/silicon nitride ($SiO_2/Si_3N_4$) deposited by CVD, a passivation layer can however also be a photosensitive polyimide or can comprise titanium nitride. Another material often used for passivation layer is phosphorous doped silicon dioxide that is typically deposited over a final layer of aluminum interconnect using a Low Temperature CVD process.

Dielectric materials find numerous applications in the formation of semiconductor devices. For instance, spacers that are formed on the sidewalls of gate electrodes can be made using silicon-nitride or silicon-oxide, BSG, PSG, polysilicon, other materials preferably of a dielectric nature, CVD oxide formed from a TEOS source. Often used are amorphous materials that inhibit the deposition of epitaxial silicon thereupon. A silicon oxide spacer can be formed via anisotropic RIE of said silicon oxide layer, using $CHF_3$ or $CF_4$—$O_2$—He as an etchant. A silicon nitride spacer can be formed via anisotropic RIE of said silicon nitride layer, using $CHF_3$ or $SF_6$—$O_2$ as an etchant.

Dielectric materials are frequently used for the creation of conductive interconnect lines, via or contact openings. In the formation of semiconductor integrated circuits, it is common practice to form interconnect metal line structures on a number of different levels within the structure and interconnecting the various levels of wiring with contact or via openings.

The first or lowest level of interconnect wires is typically formed in a layer of dielectric as a first step in the process after which a second or overlying level of interconnect wires is created in an overlying layer of dielectric over the first level.

The first level of interconnect wires is typically in contact with active regions in a semiconductor substrate but is not limited to such contact. The first level of interconnect can for instance also be in contact with a conductor that leads to other devices that form part of a larger, multi-chip structure.

The two levels of metal wires are connected by openings between the two levels, these openings are created in layers of surrounding dielectric and are filled with metal where the openings align with contact points in one or both of the levels of metal lines.

Previously used techniques to form multi-levels of wiring apply the technique of first forming the interconnect level metal in a first plane followed by forming the overlying level of interconnect wire in a second plane. This structure typically starts with the surface of a semiconductor substrate into which active devices have been created. The surface into which the pattern of interconnect lines of the first plane is formed may also be an insulation layer deposited over the surface of the substrate or a layer of oxide may first have been formed on the surface of the substrate. After the layer, into which the pattern of interconnecting wires has to be created, has been defined, the interconnecting pattern itself needs to be defined. This is done using conventional photolithographic techniques whereby the openings are made (in the layer) above the points that need to be contacted in the substrate. The openings, once created, may by lined with layers of material to enhance metal adhesion (to the sidewalls of the opening), the glue layer, or to prevent diffusion of materials into and from the substrate in subsequent processing steps, the barrier layer. For the barrier layer, a variety of materials can be used such as Ti/Tin:W (titanium/titanium nitride:tungsten), titanium-tungsten/titanium or titanium-tungsten nitride/titanium or titanium nitride or titanium nitride/titanium, silicon nitride ($Si_3N_4$), tungsten, tantalum, niobium, molybdenum. The final phase in creating the first level of interconnect lines is to fill the created openings with metal, typically aluminum, tungsten or copper, dependent on the particular application and requirements and restrictions imposed by such parameters as line width, aspect ratio of the opening, required planarity of the surface of the deposited metal and others.

This process of line formation in overlying layers of metal can be repeated in essentially the same manner as highlighted above for the first layer of interconnecting wires.

This process of forming sequential layers of interconnecting levels of wire is in many instances prone to problems and limitations. Copper has in recent times found more application in the use of metal wires due to its low resistivity, high electromigration resistance and stress voiding resistance.

Copper however exhibits the disadvantage of high diffusivity in common insulating materials such as silicon dioxide and oxygen-containing polymers. This leads to, for instance, the diffusion of copper into polyimide during high temperature processing of the polyimide resulting in severe erosion of the copper and the polyimide due to the copper combining with oxygen in the polyimide. The erosion may result in loss of adhesion, delamination, voids, and ultimately a catastrophic failure of the component.

The copper that is used in an interconnect may diffuse into the silicon dioxide layer, causing the dielectric to become conductive and also decreasing the dielectric strength of the silicon dioxide layer.

A copper diffusion barrier is therefore often required; silicon nitride is often applied as a diffusion barrier to copper. Silicon nitride however has a dielectric constant that is high compared with silicon dioxide, thereby limiting the use of silicon nitride in encapsulating copper interconnect lines.

To further enhance the adhesion of a copper interconnect line to a surrounding layer of dielectric or insulation, a seed layer is deposited over the barrier layer. A seed layer can be deposited using a sputter chamber or an Ion Metal Plasma (IMP) chamber at a temperature of between about 0 and 300 degrees C and a pressure of between about 1 and 10.0 mTorr, using copper or a copper alloy as the source at a flow rate of between about 10 and 400 sccm and using argon as an ambient gas. The minimum thickness of a seed layer is typically about 50 Angstrom, this thickness is required to achieve a reliable gap fill.

From the above highlighted applications of dielectric materials in the formation of semiconductor devices, the following performance characteristics that apply to dielectric materials are apparent:

the dielectric material must not be susceptible to moisture absorption the process of photolithographic exposure and etching of the dielectric material must be simple while no a few residual gasses remain after the etch of the dielectric has been completed the profiles of trenches or openings that are etched in the dielectric material must be well defined and readily controllable be temperature independent provide good electrical isolation (low dielectric constant) between adjacent conducting materials that are embedded in the layer of dielectric, this up to very high frequencies must provide good protection against leakage currents between adjacent conducting materials must provide high resistance against electrical voltage breakdown between adjacent conducting materials must have good adhesion to underlying layers and provide good adhesion to overlying layers, and dielectric performance must not be temperature dependent.

It is clear that a simple and dependable method, that can be used for the identification and measurement of the performance characteristics of dielectric materials, is a valuable tool in a semiconductor manufacturing environment. The invention provides such a method.

U.S. Pat. No. 5,386,507 (Teig et al.) shows a Computer graphics system for selectively modeling molecules and investigating the chemical and physical properties.

U.S. Pat. No. 6,008,906 (Maris) shows a model that uses light measurement to predict dopant concentration, trap densities, etc.

U.S. Pat. No. 5,687,090 (Chen et al.) shows a polymer simulation software that uses structural units to predict thermo-physical properties.

SUMMARY OF THE INVENTION

A principle objective of the invention is to characterize dielectric thin film properties by using chemical bonding measurements.

In accordance with the objectives of the invention a new computer based method is provided for the evaluation of dielectric film properties. These properties are for a given dielectric derived from measurements of the chemical bonding of that dielectric. Previously collected reference data are maintained in a reference data base from where data are extracted and used as input to mathematical modeling software that predicts thin film properties. The output of these prediction algorithms is used, together with chemical bonding measurements of the dielectric that is being investigated, as input to a program that computes the dielectric properties of the dielectric.

BRIEF DESCRIPTION OF THE DRAWINGS

FIG. 10 shows the weighing factors that are applied for carbon doped $SiO_2$ dielectric, as follows:

FIG. 10a shows the weighing factor applied for the Refraction Index, while

FIG. 11 addresses the dielectric constant k, FIG. 12 addresses the flat band voltage $V_{fb}$, FIG. 13 shows the weighing factor that is applied to k while FIG. 14 shows the weighing factor that is applied to $V_{fb}$.

DESCRIPTION OF THE PREFERRED EMBODIMENTS

Figure 1:
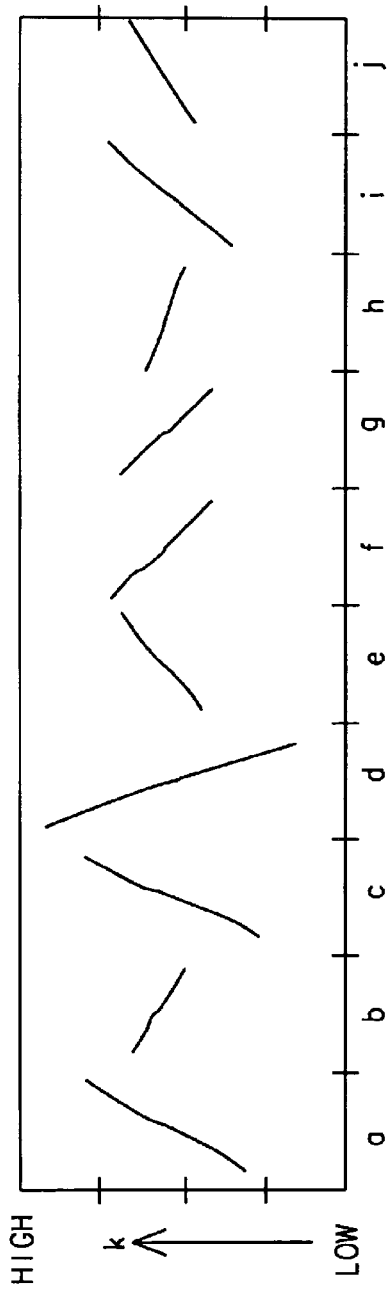
FIG. 1 shows a set of graphic presentations of the effects of CVD chemical bonding on the dielectric constant k of various dielectric materials.

FIG. 1 shows a set of graphic presentations of the effects of CVD chemical bonding on the dielectric constant k of various dielectric materials. The horizontal or X axis of the graph that is shown in FIG. 1 is subdivided in various dielectric materials, where for each of these materials is shown the effect that variation of chemical bonding has on the dielectric constant.

The various dielectric materials are represented by the sections a, b through section j along the X axis of FIG. 1. For each of the sections that are shown along the X axis, that is for a particular dielectric that is represented by that section, the dielectric chemical bonds are measured using the Fourier Transform Infrared (FTIR) method.

The vertical or Y axis of the graph represents the dielectric constant k of the various dielectric materials. The chemical bonding intensity for each material is measured by FTIR.

| X-axis section | dielectric material | wavenumber |
|---|---|---|
| a | Si—O | 450 |
| b | Si—O | 820 |
| c | Si—H | 880 |
| d | SiF | 932 |
| e | Si—O | 1050 |
| f | Si—CH$_3$ | 1243 |
| g | Si—H | 2250 |
| h | CH | 3000a |
| i | Si—NH | 3400 |
| j | OH | 3680 |

From the graph that is shown in FIG. 1, a few conclusions can be drawn:

1) chemical bonding intensity varies between different materials
2) a steeper slope of the exposure (X axis) versus k (Y axis) indicates increased sensitivity of the chemical bond to the dielectric constant (k)
3) a higher slope of the curve (k versus chemical bonding intensity) indicates that a higher bonding intensity increases the k value in the dielectric material
4) for some dielectric materials the value of k increases (and with that the value of the bonding intensity of the material) with chemical bonding intensity while for other dielectric materials the inverse is true, and
5) the rate of increase or decrease of the various curves is not uniform but varies from material to material.

Figure 2:
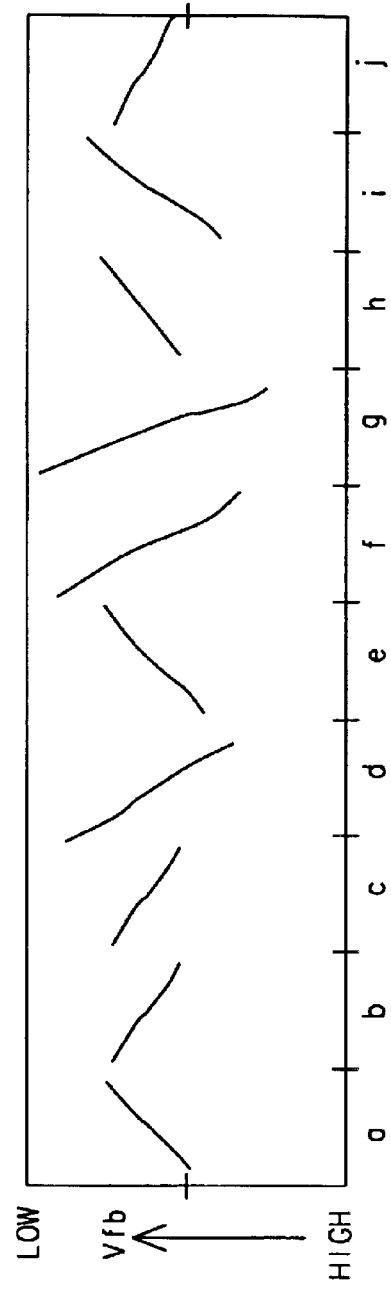
FIG. 2 shows a set of graphic presentations of the effects of CVD chemical bonding on the flat band voltage $V_{fb}$ of various dielectric materials.

FIG. 2 shows a set of graphic presentations of the effects of CVD chemical bonding on the flat band voltage $V_{fb}$ of various dielectric materials. The values and materials that are plotted along the X axis of FIG. 2 are identical to those of FIG. 1, the Y axis of FIG. 2 represents the flat band voltage $V_{fb}$ of the dielectric.

Observations can be made relative to the graphs that are shown in FIG. 2 that are similar to the previously made observations with respect to FIG. 1. It is of interest to note that, for most of the dielectric materials that are represented in FIGS. 1 and 2, the slopes of the curves of FIG. 1 and FIG. 2 for a given material are the same. This means that a dielectric material that shows for instance an increase in the value of k with chemical bonding intensity shows a corresponding increase in the value of $V_{fb}$. This is however not universally true, a fact that will become apparent by comparing sections c, h and j of FIG. 1 with like-named sections in FIG. 2. This comparison shows that, for instance, in section c of FIG. 1, the k value increases with increased chemical bonding, while the $V_{fb}$ value (as shown in FIG. 2, section c) decreases. The same is true for graphic presentations h and j, representing different dielectric materials, of respectively FIGS. 1 and 2.

Figure 3:
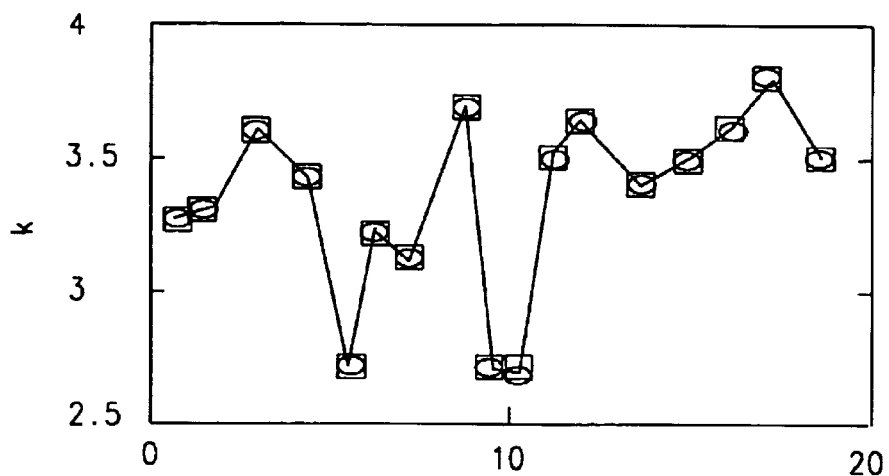
FIG. 3 shows the correlation between measured and calculated values for the dielectric constant k for carbon doped $SiO_2$.

FIG. 3 shows the correlation between measured and calculated values for the dielectric constant k of carbon doped $SiO_2$ dielectric material. The measured values of the dielectric constant k are plotted along the Y axis as rectangles while the values for k that are calculated in accordance with the method of the invention are plotted along the Y axis with circles. The individual wafers that have been used for the subject evaluation are listed by sequence number along the X axis, in other words one particular point along the X axis is one wafer (in the sequence number in which the various wafers were analyzed), for that wafer the measured and predicted values of k have been plotted along the Y axis. It is apparent from the values that are indicated in FIG. 3 that the correlation between measured and calculated values is excellent.

Figure 4:
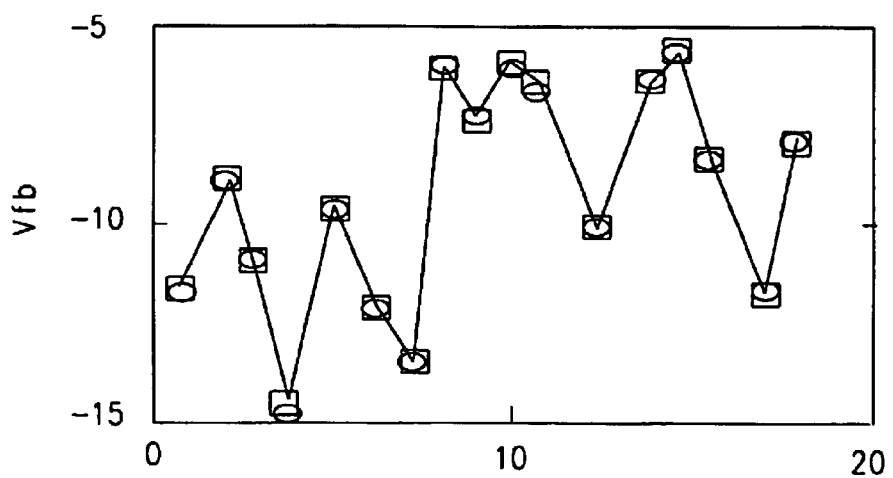
FIG. 4 shows the correlation between measured and calculated values for the flat band voltage $V_{fb}$ for carbon doped $SiO_2$.

FIG. 4 shows the correlation between measured and calculated values for the flat band voltage $V_{fb}$ of carbon doped $SiO_2$ dielectric material. The measured values of the flat band voltage $V_{fb}$ are indicated by rectangles in FIG. 4 while the values for the flat band voltage $V_{fb}$ that are calculated in accordance with the method of the invention are indicated with circles. The individual wafers that have been used for the subject evaluation are listed by sequence number along the X axis, in other words one particular point along the X axis is one wafer (in the sequence number in which the various wafers were analyzed), for that wafer the measured and predicted values of k have been plotted along the Y axis. It is apparent from the values that are indicated in FIG. 4 that the correlation between measured and calculated values is excellent.

Figure 5:
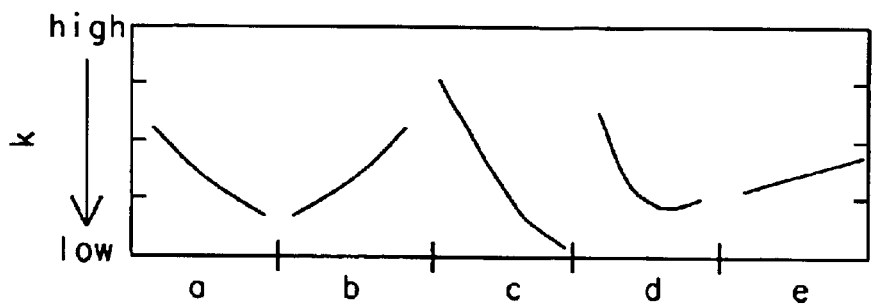
FIG. 5 shows the effects of CVD chemical bonding on the dielectric constant k of carbon doped $SiO_2$ dielectric.

FIG. 5 shows the effects of chemical bonding on the dielectric constant k of carbon doped $SiO_2$ dielectric material.

FIG. 5 shows, similar to FIG. 1, a set of graphic presentations of the effects of CVD chemical bonding on the dielectric constant k of various carbon doped $SiO_2$ dielectric materials.

The horizontal or X axis of the graph that is shown in FIG. 5 is subdivided into various carbon doped $SiO_2$ dielectric materials, where for each of these materials is shown the effect that modified chemical bonding has on the dielectric constant.

The vertical or Y axis of the graph represents the dielectric constant k of the various carbon doped $SiO_2$ dielectric materials. The chemical bonding for each carbon doped $SiO_2$ material is measure by FTIR. The list of materials and wavenumbers is as follows:

| X-axis section | dielectric material | wavenumber |
|---|---|---|
| a | SiC, SiO, CH | 800 |
| b | SiO | 1030 |
| c | $SiCH_3$ | 1268 |
| d | SiH | 2184 |
| e | CH | 3000 |

From the graph that is shown in FIG. 5 the conclusion that can be drawn is that different chemical bonding intensities affect the dielectric constant (k). As some of the chemical bonding intensities increase, the k value can increase. Some chemical bonding intensities however can decrease the value of k as the chemical bonding intensities increase.

Figure 6:
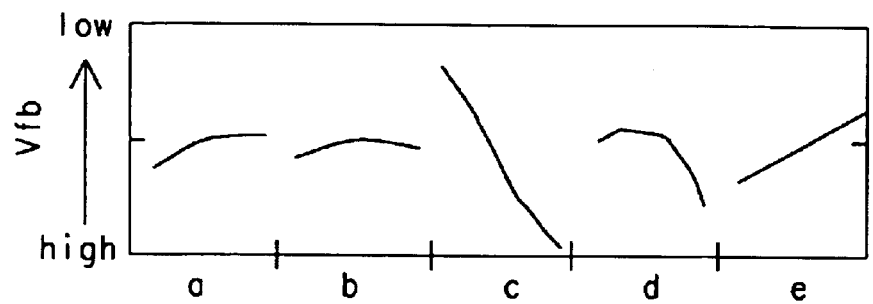
FIG. 6 shows the effects of CVD chemical bonding on the flat band voltage $V_{fb}$ of carbon doped $SiO_2$ dielectric.

FIG. 6 shows a set of graphic presentations of the effects of CVD chemical bonding on the flat band voltage $V_{fb}$ of various carbon doped $SiO_2$ dielectric materials. The values and materials that are plotted along the X axis of FIG. 6 are identical to those of FIG. 5, the Y axis of FIG. 6 represents the flat band voltage $V_{fb}$ of the dielectric. Observations can be made relative to the graphs that are shown in FIG. 6 that are similar to the previously made observations with respect to FIG. 5.

Figure 7:
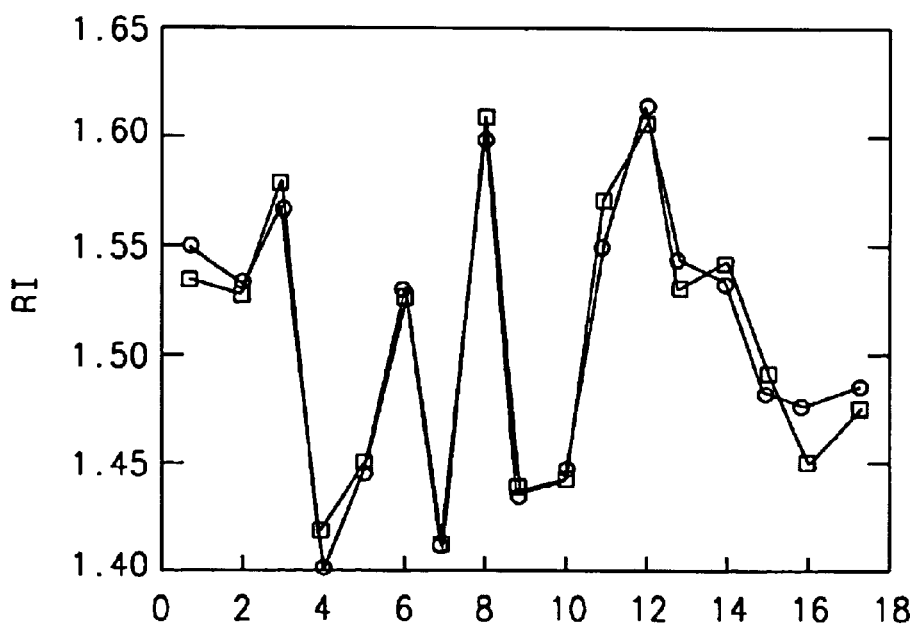
FIG. 7 shows a correlation between measured values and predicted values for the Refraction Index (RI) of carbon doped $SiO_2$ dielectric.

FIG. 7 shows a correlation between measured values and predicted values using the method of the invention for the Refraction Index (RI) of carbon doped $SiO_2$ dielectric. The measured values of RI are indicated by rectangles in FIG. 7 while the values for RI that are calculated in accordance with the method of the invention are indicated with circles. The individual wafers that have been used for the subject evaluation are listed by sequence number along the X axis, in other words one particular point along the X axis is one wafer (in the sequence number in which the various wafers were analyzed), for that wafer the measured and predicted values of k have been plotted along the Y axis. It is apparent from the values that are indicated in FIG. 7 that the correlation between measured and calculated values of RI is excellent.

Figure 8:
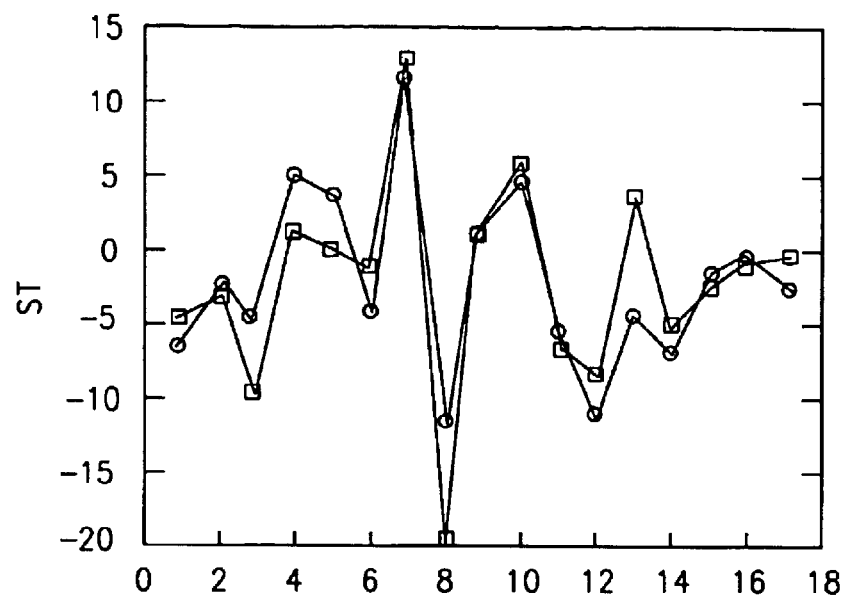
FIG. 8 shows a correlation between measured values and predicted values for the Stress (ST) factor of carbon doped $SiO_2$ dielectric.

FIG. 8 shows a correlation between measured values and predicted values for the Stress factor of carbon doped $SiO_2$ dielectric. The measured values of Stress (ST) are plotted along the Y axis and are indicated by rectangles in FIG. 8 while the values for ST that are calculated in accordance with the method of the invention are plotted along the Y axis and are indicated with circles. The individual wafers that have been used for the subject evaluation are listed by sequence number along the X axis, in other words one particular point along the X axis is one wafer (in the sequence number in which the various wafers were analyzed), for that wafer the measured and predicted values of k have been plotted along the Y axis. It is apparent from the values that are indicated in FIG. 8 that the correlation between measured and calculated values of ST is excellent.

Figure 9:
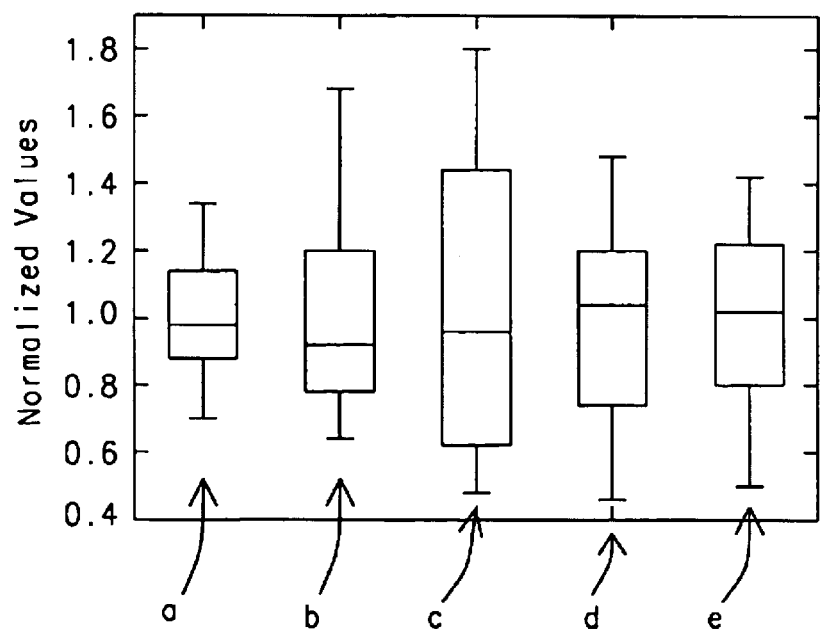
FIG. 9 shows the chemical bonding normalized values of carbon doped $SiO_2$ dielectric.

FIG. 9 shows the normalized values of carbon doped $SiO_2$ dielectric. The various normalization factors that are applied under the method of the invention relate to the conditions that have been detailed in FIGS. 5 and 6 above, that is normalization conditions highlighted with "a" are the normalization conditions that apply for SiC, SiO, Ch exposed with infrared of 800 MHz. The normalization conditions that are highlighted in FIG. 9 as "b", "c", "d" and "e" correspondingly relate to the conditions that are highlighted as such in FIGS. 5 and 6.

Figure 10A:
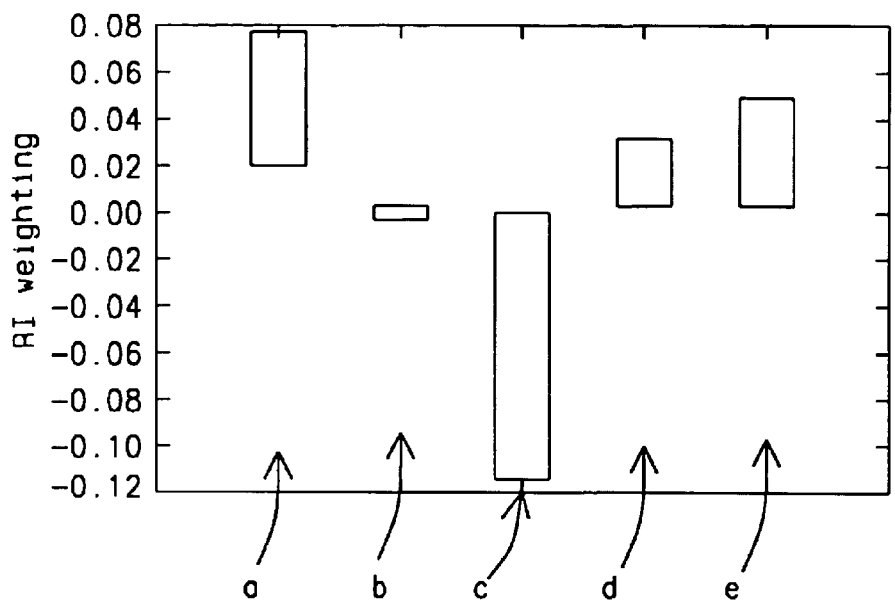

FIG. 10 shows the weighing factors that are applied for carbon doped $SiO_2$ dielectric using the method of the invention, as follows:

FIG. 10a shows the weighing factor applied for the Refraction Index (RI), while

Figure 10B:
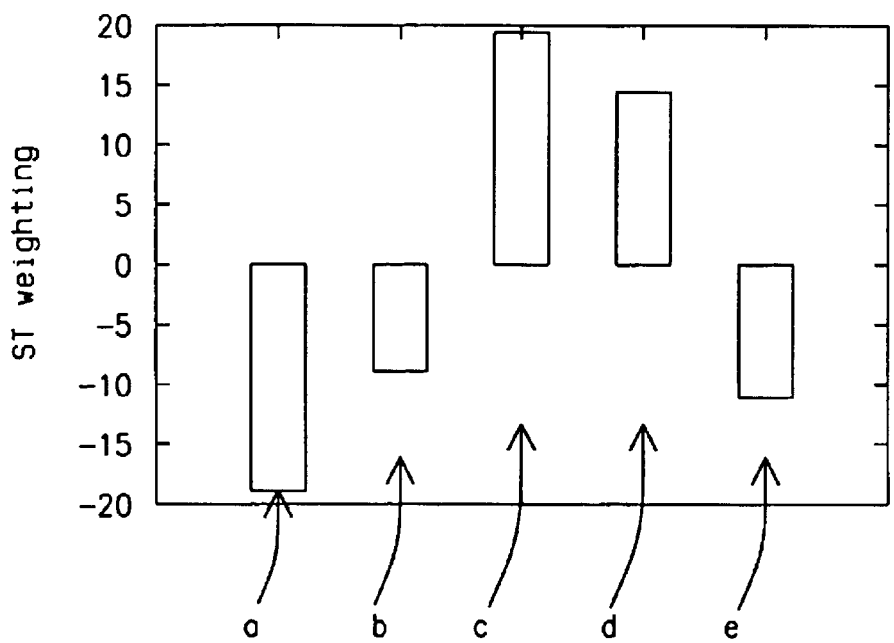
FIG. 10b shows the weighing factor applied for the Stress factor.

FIG. 10b shows the weighing factor applied for the Stress (ST) factor.

The regions that are highlighted with "a", "b", "c", "d" and "e" refer to the same conditions of dielectric material that have previously been highlighted under FIGS. 5, 6 and 9.

Figure 11:
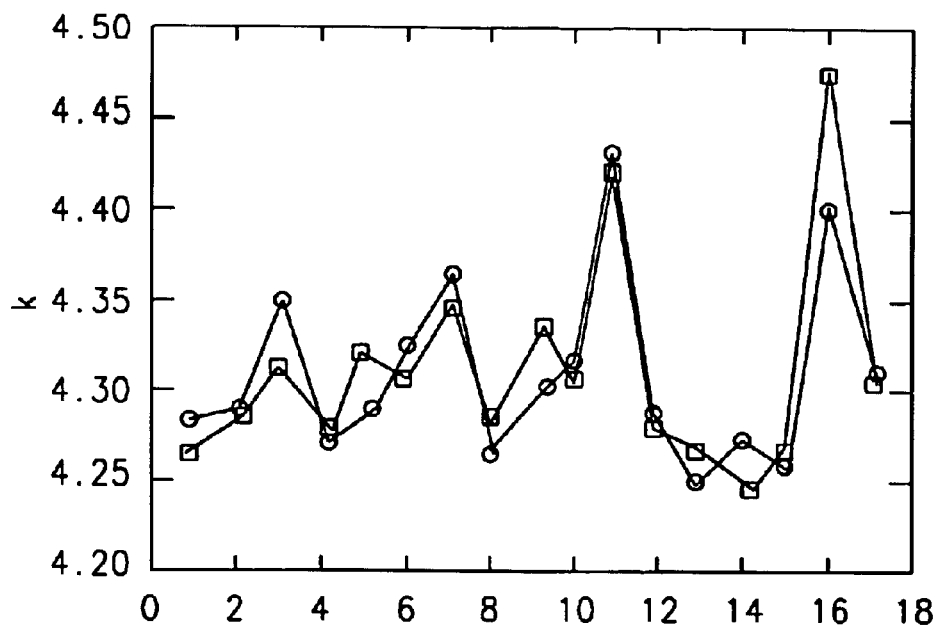
FIGS. 11 through 14 show the correlation between chemical bonding and electrical properties of a dielectric, this for both the measured correlation and the predicted correlation.
Figure 12:
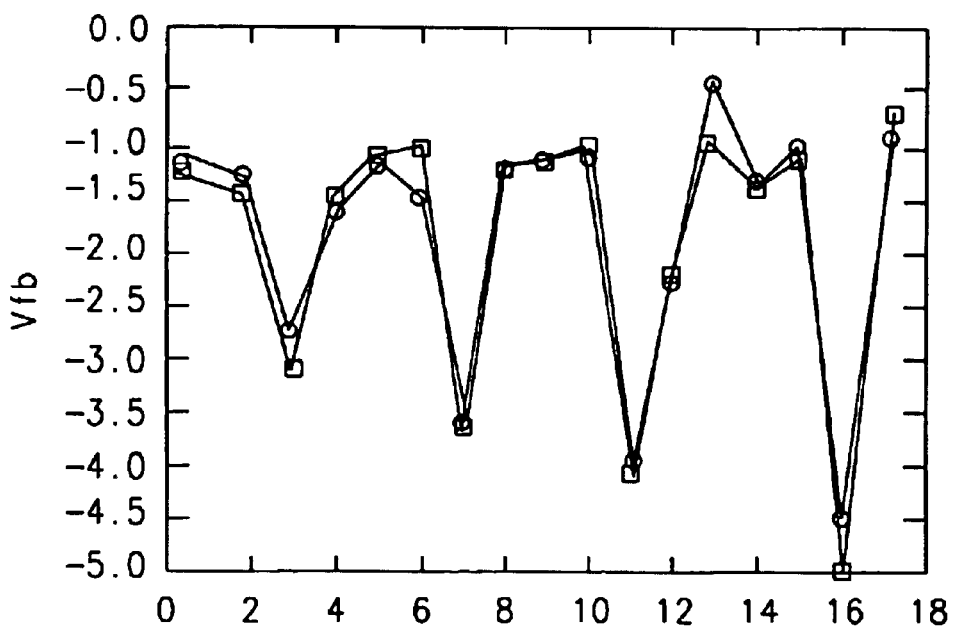
Figure 13:
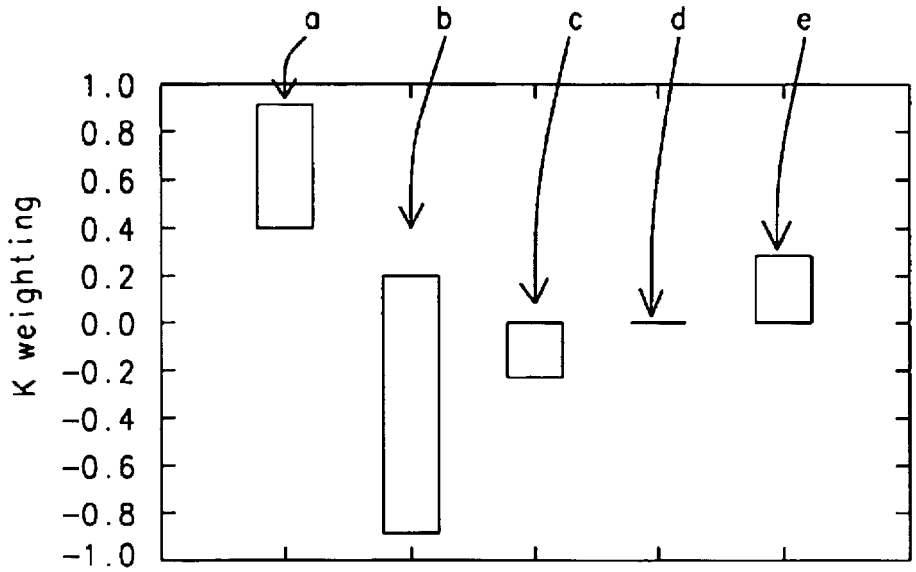
Figure 14:
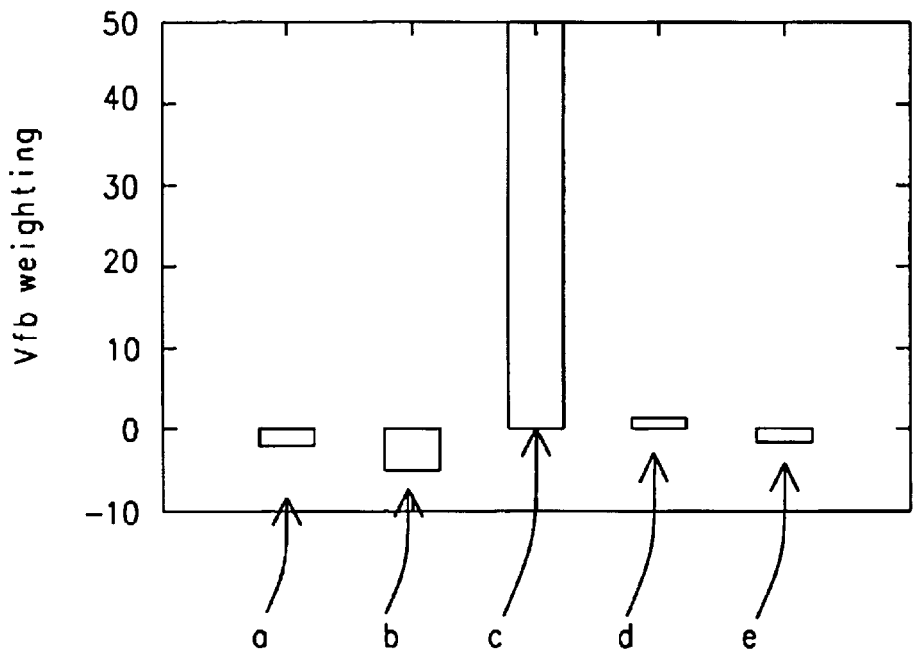

FIGS. 11 through 14 show the correlation between chemical bonding and electrical properties of a dielectric, this for both the measured correlation and the predicted correlation. FIG. 11 addresses the dielectric constant k, FIG. 12 addresses the flat band voltage $V_{fb}$, FIG. 13 shows the weighing factor that is applied to k while FIG. 14 shows the weighing factor that is applied to $V_{fb}$. The individual wafers that have been used for the subject evaluation are listed by sequence number along the X axis, in other words one particular point along the X axis is one wafer (in the sequence number in which the various wafers were analyzed), for that wafer the measured and predicted values of k have been plotted along the Y axis. It can again be concluded that the correlation that is shown in FIGS. 11 and 12 is very good correlation between the measured and the predicted values for both k and $V_{fb}$. The weighing factors that are shown have been applied to a selected list of dielectric materials that are selected from the dielectric materials that have first been shown under FIG. 1, as follows:

| highlighted | dielectric material | wavenumber |
|---|---|---|
| a | Si—O | 450 |
| b | Si—O | 820 |
| c | Si—O | 1050 |
| d | Si—$CH_3$ | 1243 |
| e | CH | 3000 |

Figure 15:
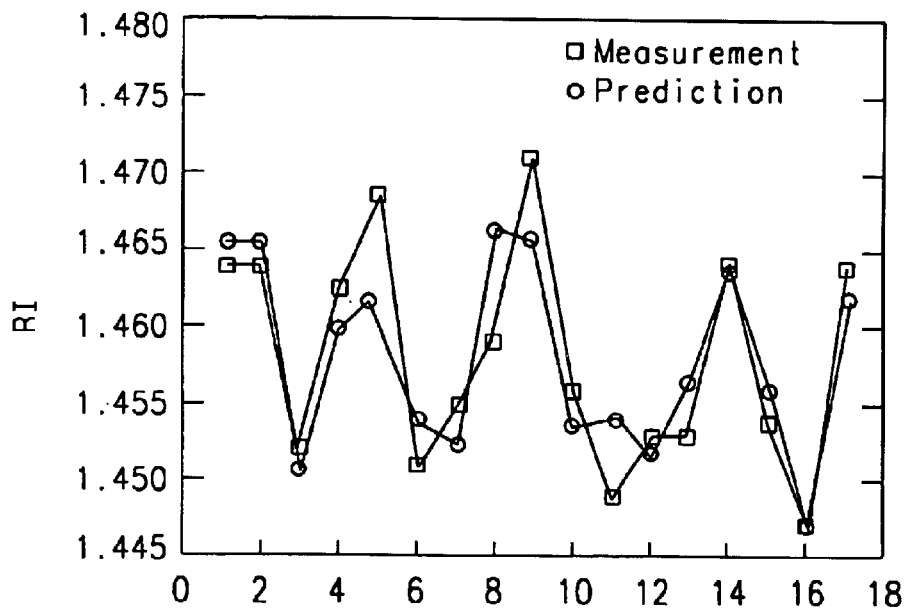
FIG. 15 shows TEOS characterization, RI measured versus predicted.
Figure 16:
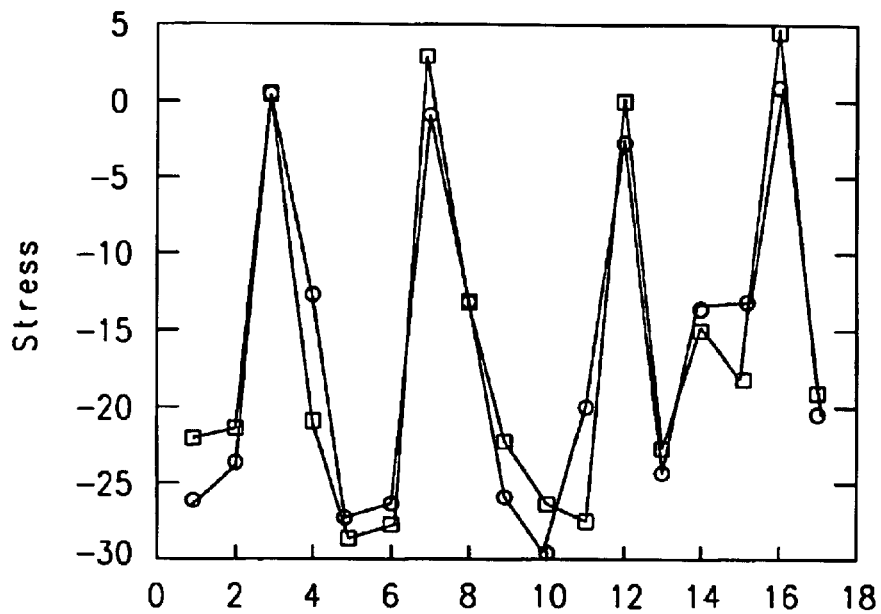
FIG. 16 shows TEOS characterization, Stress measured versus predicted.

FIGS. 15 and 16 address a practical verification of the method of the invention by evaluating the correlation for RI and Stress of a layer of TEOS, the correlation is between measured values for these parameters and predicted values for these parameters in accordance with the method of the invention. FIG. 15 shows TEOS characterization, RI measured versus predicted. The measured values of RI are indicated by rectangles in FIG. 15 while the values for RI that are calculated in accordance with the method of the invention are indicated with circles. FIG. 16 shows TEOS characterization, Stress measured versus predicted. It is apparent from the values that are indicated in FIGS. 15 and 16 that the correlation between measured and calculated values of RI for TEOS is excellent. The X axis serves the same function as previously has been highlighted, that is to indicated the various wafers that have been analyzed for the stated purpose.

Figure 17:
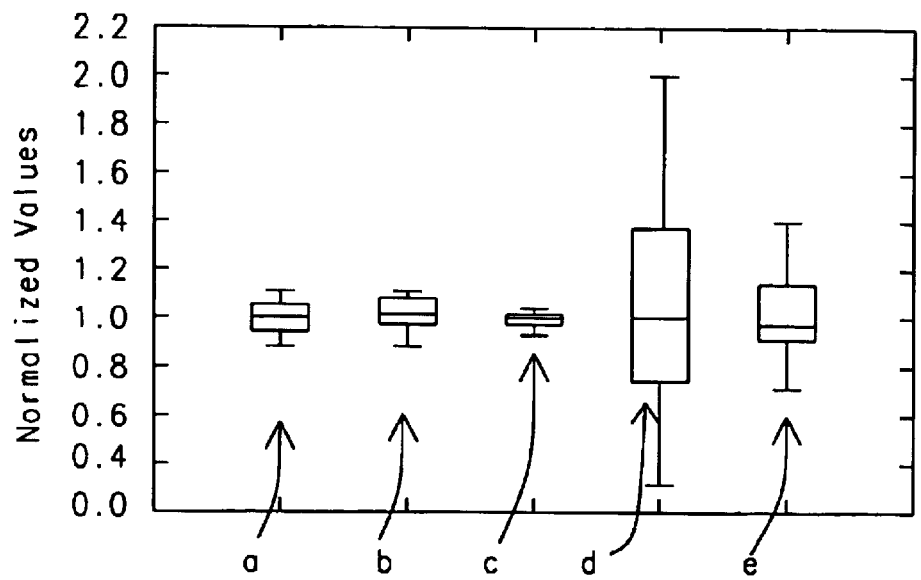
FIG. 17 shows the normalized values for the TEOS dielectrics.

FIG. 17 shows the normalized values for the TEOS dielectrics. The various normalization factors and weighing factors that are applied in FIG. 17 under the method of the invention relate to the conditions that have been detailed in FIG. 13 above, that is normalization conditions highlighted with "a" are the normalization conditions that apply for Si—O exposed with infrared of 450 wavenumber. The normalization conditions that are highlighted in FIG. 17 as "b", "c", "d" and "e" Correspondingly relate to the conditions that are highlighted as such in FIG. 13.

Figure 18A:
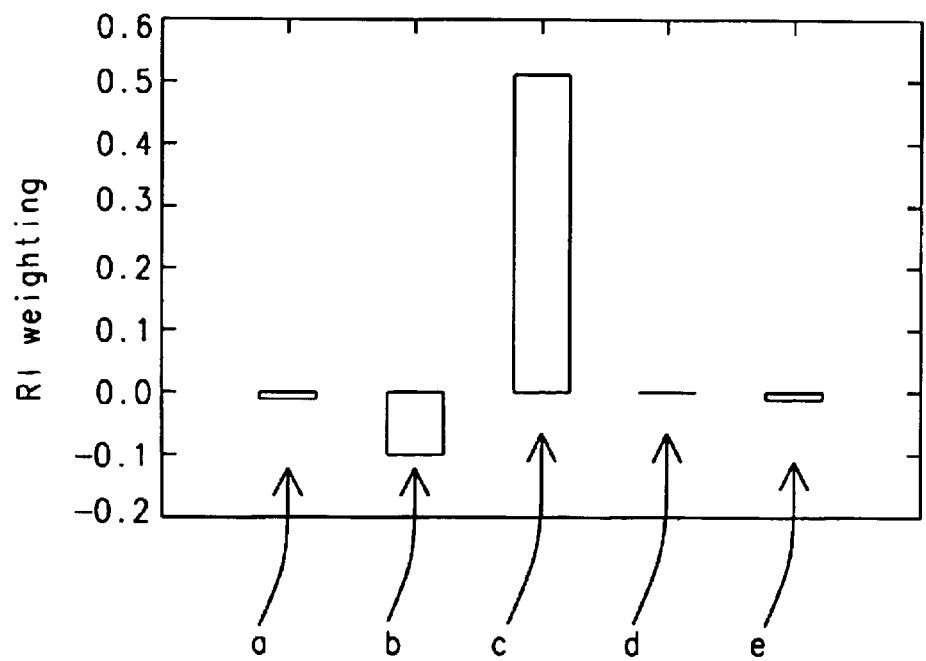
FIG. 18a a shows the RI weighing applied to the TEOS dielectrics.

FIG. 18 shows the weighing factors that are applied for TEOS dielectrics using the method of the invention, as follows:

FIG. 18a shows the weighing factor applied for the Refraction Index, while

Figure 18B:
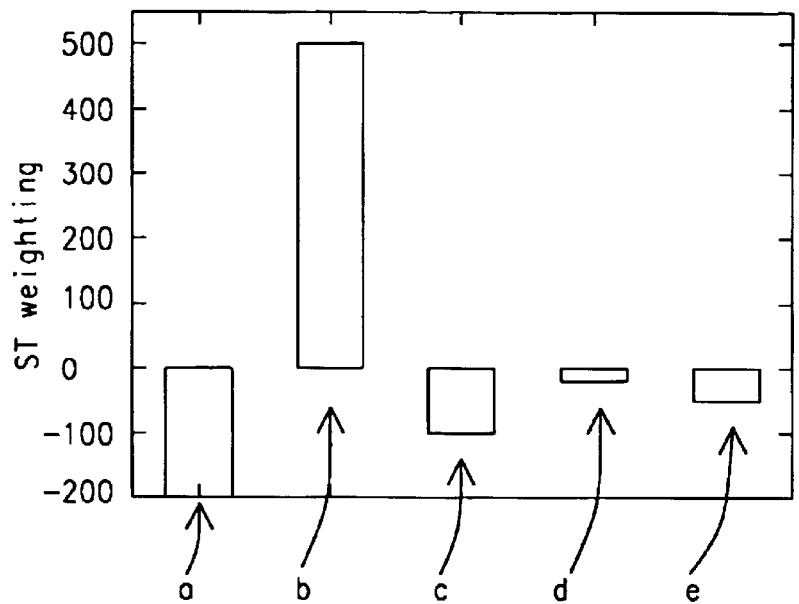
FIG. 18b a shows the Stress weighing applied to the TEOS dielectrics.

FIG. 18b shows the weighing factor applied for the Stress factor.

The weighing factors that are highlighted in FIGS. 18a and 18b as "a", "b", "c", "d" and "e" relate to the conditions of materials that are highlighted as such under FIG. 13.

Figure 19:
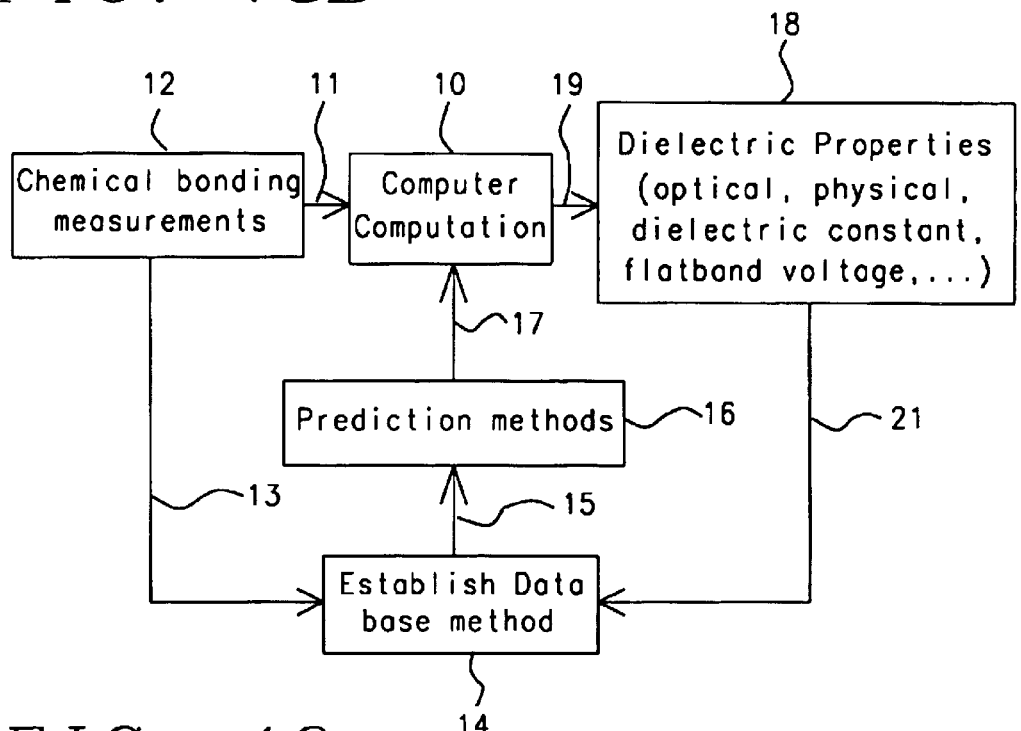
FIG. 19 shows a block diagram of the computational method of the invention.

FIG. 19 shows a block diagram of the computational method of the invention.

It should from the previous discussions be clear that there is a close and definite relationship between chemical bonding properties of a dielectric and their electrical properties, this is for instance clear from the correlation that has been established between these two entities as shown in FIGS. 11 and 12. The effects that chemical bonding has on dielectric performance characteristics such as the dielectric constant k and the flat band voltage $V_{fb}$ of the dielectric has also been established, see for instance FIGS. 1 and 2. Once the chemical bonding of a dielectric film is known, other characteristics of this dielectric film such as the dielectric constant k and $V_{fb}$ can be derived from which dielectric characterization parameters such as the Refraction Index and the Stress Coefficient can be Calculated. It is this interdependence between the various parameters that characterize a layer of dielectric that is used for the computational model of the invention. This computational model is highlighted in FIG. 19. The even numbered entities that are highlighted in FIG. 19 are software packages or programs that are computer based, the odd numbered entities are interconnects between the various functions of the computational model which henceforth will be referred to as a Dielectric Analysis Program (DAP).

The central function of the DAP system is function 10, the Dielectric Property Computation (DPC) program. Input to this program are the Chemical Bonding Measurements 12 that are provided to the DPC function 10 by means of interface 11. Interface 11 can be any currently available method of, among other functions, accessing a program and providing data to or extracting data from that program. Further input to the DPC function 10 is the output of the Behavioral Prediction Algorithms (BPA) function 16, this input is provided to DPC function 10 by means of the interconnect 17. The Established Data Base 14 is the central repository of data that relates to dielectric materials and there depositions, such as previously have been highlighted. This data base 14 is updated with any data that has been obtained during the execution of the DAP functions, key among these data are CBM data 12 (supplied to the EDB via link 13) that have been obtained for a deposited layer of dielectric while dielectric properties 18 that have been obtained by the DAP system for a given layer of dielectric are stored (supplied to the EDB via link 21) and maintained in data base 14 for future reference. This data may also be accessed via link 15 as input to the BPA function 16. Output link 19 provides the predicted Dielectric Properties 18 to a ultimate user of the DAP functions.

Although the invention has been described and illustrated with reference to specific illustrative embodiments thereof, it is not intended that the invention be limited to those illustrative embodiments. Those skilled in the art will recognize that variations and modifications can be made without departing from the spirit of the invention. It is therefore intended to include within the invention all such variations and modifications which fall within the scope of the appended claims and equivalents thereof.

What is claimed is:

1. A method of digital processing for:
predicting thin film dielectric properties, comprising:
a reference data base;
measuring chemical bonding parameters of said thin film dielectric, said measuring chemical bonding parameters comprising Fourier Transform Infrared (FTIR) analysis;
software based algorithms predicting thin film behavioral characteristics based on thin film parameters;
a software based function combining said chemical bonding parameters with said predicted thin film behavioral characteristics, thereby predicting dielectric properties of said thin film;
a data interconnect between said reference data base and said software based algorithms;
a data interconnect between said software based algorithms and said software based function combining said chemical bonding parameters with said predicted thin film behavioral characteristics;
an output medium for outputting said predicted dielectric properties of said thin film;
an input medium to said reference data base for supplying said predicted dielectric properties of said thin film to said reference data base; and
an input medium to said reference data base for supplying said measured chemical bonding parameters of said thin film dielectric of said thin film to said reference data base.

2. The method of claim 1, wherein said chemical bonding parameters comprising user defined attributes defining said thin film dielectric.

3. The method of claim 1, said reference data base comprising data segments for defining thin film dielectrics, said reference data base comprising an indication of different types of data defining thin film dielectrics.

4. The method of claim 1 wherein said input medium to said reference data base for supplying said predicted dielectric properties and said input medium to said reference data base for supplying said measured chemical bonding parameters of said thin film dielectric stores different stages of calculation results in said reference library, whereby said behavioral prediction algorithms use stored values of the measured chemical bonding parameters and said predicted dielectric properties.

5. The method of claim 1, said behavioral prediction algorithm comprising mixing and splitting rules predicting at least one mixing and splitting of thin film dielectric prediction.

6. An apparatus of a digital processor for predicting thin film dielectric properties, comprising:

input means for enabling user definition of a desired thin film dielectric formed of a multiplicity of streams of data elements, including at least one thin film dielectric component, said user definition comprising chemical bonding measurements, said chemical bonding measurements having been performed using Fourier Transform Infrared (FTIR) analysis;

a data assembly coupled to said input means for holding data of the desired thin film dielectric, for each thin film dielectric the data assembly representing the thin film dielectric as a collection of segments and a set of attributes, the collection of segments and set of attributes defining the thin film dielectric, the data assembly utilizing an attribute set table that provides thin film dielectric characteristics in a standardized manner from one thin film dielectric to another and provides distribution function information for describing thin film dielectric properties, such that said table specifies properties of one or more thin film dielectrics to support predicting of a variety of thin film dielectrics;

means for placing and holding data of the desired thin film dielectric in said data assembly coupled to said input means for each thin film dielectric; and processor means for predicting thin film dielectric properties by mathematically modeling stream flow and element operation of the thin film dielectric whereby the mathematical modeling includes predicting thin film properties and attributes values of the thin film dielectric, based on said distribution functions, said data using data stored in said data assembly according to the attribute set table.

7. The apparatus of claim 6, said user definition of a desired thin film dielectric comprising chemical bonding measurements for at least one thin film dielectric.

8. The apparatus of claim 6, said user definition of a desired thin film dielectric further comprising user defined attributes for further definition of said thin film dielectric.

9. The apparatus of claim 6, wherein said data assembly comprising segments for defining a thin film dielectric and, for a thin film dielectric, comprising an indication of the segments defining said thin film dielectric.

10. The apparatus of claim 6, wherein said processing means for predicting thin film dielectric properties storing calculation results of different stages of calculation, such that during mathematical modeling of each stream, the processor means uses stored values of a collection of segments and a set of attributes of a thin film dielectric as held in said data assembly.

11. The apparatus of claim 6 wherein said processor means further utilizes mixing and splitting rules to mathematically predict at least one mixing and splitting of streams.

12. The apparatus of claim 6 with the addition of the means to place and hold predicted data of the desired thin film dielectric in said data assembly coupled to an input means to said data assembly for each thin film dielectric.

13. A method applied using a digital processor for predicting thin film dielectric properties, comprising:

providing input means to the digital processor for enabling user definition of a desired thin film dielectric formed of a multiplicity of streams of data elements, including at least one thin film dielectric component, said user definition comprising chemical bonding measurements, said chemical bonding measurements having been performed using Fourier Transform Infrared (FTIR) analysis;

providing a data assembly coupled to said input means for holding data of the desired thin film dielectric, for each thin film dielectric the data assembly representing the thin film dielectric as a collection of segments and a set of attributes, the collection of segments and set of attributes defining the thin film dielectric, the data assembly utilizing an attribute set table that provides thin film dielectric characteristics in a standardized manner from one thin film dielectric to another and provides distribution function information for describing thin film dielectric properties, such that said table specifies providing properties of one or more thin film dielectrics to support predicting of a variety of thin film dielectrics;

providing processor means for predicting thin film properties by mathematically modeling stream flow and element operation of the thin film dielectric whereby the mathematical modeling includes predicting thin film properties and attributes values of the thin film dielectric, based on said distribution functions, said data using data stored in said data assembly according to the attribute set table; and providing the means to place and hold predicted data of the desired thin film dielectric in said data assembly coupled to providing an input means to said data assembly for each thin film dielectric.

14. The method of claim 13, said user definition of a desired thin film dielectric comprising chemical bonding measurements that indicate and for at least one thin film dielectric.

15. The method of claim 13, said user definition of a desired thin film dielectric comprising user defined attributes of said thin film dielectric.

16. The method of claim 13, said data assembly comprising segments for defining a thin film dielectric, comprising an indication of the segments defining said thin film dielectric.

17. The method of claim 13, said processing means storing calculation results of different stages of calculation, such that during mathematical modeling of each stream, the processor means uses stored values of a collection of segments and a set of attributes of each thin film dielectric as held in said data assembly.

18. The method of claim 13 wherein said processor means further utilizes mixing and splitting rules to mathematically predict at least one mixing and splitting

* * * * *

UNITED STATES PATENT AND TRADEMARK OFFICE
CERTIFICATE OF CORRECTION

PATENT NO. : 6,836,693 B1
DATED : December 14, 2004
INVENTOR(S) : Toshihiro

It is certified that error appears in the above-identified patent and that said Letters Patent is hereby corrected as shown below:

Column 2,
Line 19, "position--which" should read -- position which --,
Line 25, "the" should read -- in --, and
Line 44, "etc." should read -- etc., --.

Column 6,
Line 33, "terminal etc." should read -- terminal, etc., --.

Column 9,
Line 36, "etc." should read -- etc., --.

Column 10,
Line 44, "on side" should read -- on the side --, and
Line 47, "can decreased." should read -- can be decreased. --.

Column 13,
Line 32, "angel" should read -- angle --.

Column 14,
Line 47, "of," should read -- of: --.

Column 15,
Line 31, "body" should read -- body, --.

Column 16,
Line 19, "an" should read -- a --, and
Line 58, "decreased." should read -- be decreased. --.

Column 18,
Line 12, "comprises" should read -- comprise --,
Line 34, "comprises" should read -- comprised --,
Line 36, "comprises by" should read -- comprised of --, and
Line 37, "etc." should read -- etc., --.

Column 22,
Line 59, "etc." should read -- etc., --.

Column 23,
Line 41, "can decreased." should read -- can be decreased. --.

UNITED STATES PATENT AND TRADEMARK OFFICE
CERTIFICATE OF CORRECTION

PATENT NO. : 6,836,693 B1
DATED : December 14, 2004
INVENTOR(S) : Toshihiro

It is certified that error appears in the above-identified patent and that said Letters Patent is hereby corrected as shown below:

Column 27,
Line 40, "on side" should read -- on the side --.

Column 29,
Lines 54 and 57, "comprising:" should read -- comprising --.

Column 30,
Lines 5, 41 and 46, "comprising:" should read -- comprising --.

Signed and Sealed this

Seventeenth Day of May, 2005

JON W. DUDAS
*Director of the United States Patent and Trademark Office*

UNITED STATES PATENT AND TRADEMARK OFFICE
CERTIFICATE OF CORRECTION

PATENT NO.   : 6,836,693 B1
DATED        : December 28, 2004
INVENTOR(S)  : Hung-Wen Chiou It is certified that error appears in the above-identified patent and that said Letters Patent is hereby corrected as shown below:

This certificate supersedes Certificate of Correction issued May 17, 2005, the number was erroneously mentioned and should be vacated since no Certificate of Correction was granted.

Signed and Sealed this

Fifth Day of July, 2005

JON W. DUDAS
*Director of the United States Patent and Trademark Office*